(12) United States Patent
Inomata et al.

(10) Patent No.: US 8,535,697 B2
(45) Date of Patent: Sep. 17, 2013

(54) COSMETIC COMPOSITION

(75) Inventors: Yukio Inomata, Sumida-ku (JP); Toshio Uesaka, Sumida-ku (JP); Satoshi Sugawara, Sumida-ku (JP); Yasumitsu Sakuma, Wakayama (JP); Masahiro Umehara, Wakayama (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 12/091,064

(22) PCT Filed: Nov. 17, 2006

(86) PCT No.: PCT/JP2006/323514
§ 371 (c)(1),
(2), (4) Date: Apr. 22, 2008

(87) PCT Pub. No.: WO2007/058382
PCT Pub. Date: May 24, 2007

(65) Prior Publication Data
US 2009/0263433 A1 Oct. 22, 2009

(30) Foreign Application Priority Data

Nov. 18, 2005 (JP) ................................ 2005-334283

(51) Int. Cl.
*A61K 8/02* (2006.01)
*A61K 8/00* (2006.01)
*A61K 8/18* (2006.01)
*A61K 31/695* (2006.01)
*A61Q 17/04* (2006.01)
*A61Q 5/12* (2006.01)
*A01N 55/00* (2006.01)

(52) U.S. Cl.
USPC ............. 424/401; 424/59; 424/70.12; 514/63

(58) Field of Classification Search
USPC ........................... 424/401, 59, 70.12; 514/63
See application file for complete search history.

(56) References Cited

U.S. PATENT DOCUMENTS

| | | | |
|---|---|---|---|
| 4,029,622 A * | 6/1977 | Keller et al. ................... | 524/369 |
| 4,906,458 A | 3/1990 | Shigeta et al. | |
| 5,188,831 A | 2/1993 | Nicoll et al. | |
| 5,725,844 A * | 3/1998 | Gers-Barlag et al. ............ | 424/59 |
| 2002/0077372 A1* | 6/2002 | Gers-Barlag et al. ............ | 516/98 |
| 2004/0241126 A1 | 12/2004 | Sakuta | |
| 2005/0008600 A1 | 1/2005 | Nakanishi et al. | |

FOREIGN PATENT DOCUMENTS

| | | |
|---|---|---|
| DE | 195 48 015 | 6/1997 |
| EP | 0 780 112 | 6/1997 |
| EP | 0 953 336 | 11/1999 |
| JP | A-6-16527 | 1/1994 |
| JP | A-8-506574 | 7/1996 |
| JP | 9-175934 | 7/1997 |
| JP | 9-175973 | 7/1997 |
| JP | 11 180820 | 7/1999 |
| JP | 2001354515 A * | 12/2001 |
| JP | 2004285026 A * | 10/2004 |
| JP | 2004-346046 | 12/2004 |
| JP | 2005-42097 | 2/2005 |
| WO | 96 28137 | 9/1996 |

OTHER PUBLICATIONS

U.S. Appl. No. 12/089,611, filed Apr. 9, 2008, Inomata, et al.

* cited by examiner

*Primary Examiner* — Layla Soroush
(74) *Attorney, Agent, or Firm* — Oblon, Spivak, McClelland, Maier & Neustadt, L.L.P.

(57) ABSTRACT

Provided are a cosmetic composition which is an $O_1/W/O_2$ emulsion composition and contains, in the oil phases $O_1$ and $O_2$ thereof, fine metal oxide particles having ultraviolet screening ability; and a preparation process of the cosmetic composition.

12 Claims, No Drawings

COSMETIC COMPOSITION

CROSS REFERENCES TO RELATED APPLICATIONS

This application is a 371 of International Patent Application No. PCT/JP2006/323514, filed on Nov. 17, 2006, and claims priority to Japanese Patent Application No. 2005-334283, filed on Nov. 18, 2005.

TECHNICAL FIELD

The present invention relates to an ultraviolet protection cosmetic composition having high ultraviolet protection effects and at the same time, having excellent water resistance.

BACKGROUND ART

Ultraviolet rays reaching the Earth's surface from the sun can be classified into long wave ultraviolet rays UVA (from 320 to 400 nm) and medium wave ultraviolet rays UVB (from 280 to 320 nm). UVA can be classified further into UVAII (from 320 to 340 nm) and UVAI (from 340 to 400 nm). Even brief exposure to UVB causes sunburn, inflammation of the skin such as erythema and edema and several days later, it leads to pigmentation. Thus, UVB has a tanning action. Moreover, UVB is said to induce skin aging and cancer. Exposure to UVA, on the other hand, changes a pale-color melanin pigment existing in the epidermis into a dark-color melanin pigment and thereby darkens the skin, which phenomenon is called "immediate pigment darkening". In addition, UVA is said to reduce resilience or elasticity of the skin.

Sunscreen cosmetic compositions containing an organic ultraviolet absorber capable of efficiently absorbing ultraviolet light or ultraviolet protection powders capable of scattering ultraviolet light have been employed in order to protect the skin from ultraviolet light. Many sunscreen cosmetic compositions which have recently been put on the market are W/O types having long lasting ultraviolet protection effects and is easily applicable to the skin. Their ultraviolet protection effects are obtained by incorporating, in an outer oil phase of such emulsions, an organic ultraviolet absorber or ultraviolet protection powders (hydrophobic ultraviolet protection powders) having a surface subjected to hydrophobic treatment in combination.

In these emulsions, however, an ultraviolet protection agent is present only in one phase (oil phase) so that the ultraviolet protection agent cannot be applied to the skin uniformly. As a result, the agent often fails to fully produce its effects.

Various investigations have been made with a view to attaining more uniform distribution of an ultraviolet protection agent on the skin when an emulsion composition containing it is applied to the skin. For example, it is described in Patent Document 1 that use of water-dispersible ultrafine titanium dioxide and oil-dispersible ultrafine titanium dioxide in combination enables more uniform distribution of the ultraviolet protection agents on the skin, thereby synergistically improving protection from ultraviolet light.

In Patent Document 2, it is described that the combined use of an oil soluble ultraviolet absorber and a water soluble ultraviolet absorber enables improvement of ultraviolet protection effects.

These compositions however have insufficient resistance to sweat or water because of the water soluble ultraviolet protection agent contained therein and they are not satisfactory in the maintenance of ultraviolet protection effects.

[Patent Document 1] JP-A-6-16527
[Patent Document 2] JP-A-8-506574

DISCLOSURE OF THE INVENTION

In the present invention, there is thus provided a cosmetic composition which is an $O_1/W/O_2$ emulsion composition and containing, in each of oil phases $O_1$ and $O_2$ thereof, fine metal oxide particles having ultraviolet screening ability; and a preparation process of the composition.

BEST MODE FOR CARRYING OUT THE INVENTION

The present invention relates to an ultraviolet protection cosmetic composition having high ultraviolet protection effects and at the same time, having excellent water resistance when applied to the skin.

The present inventors have found that an ultraviolet protection cosmetic composition which is in the form of an O/W/O multilayer emulsion and has improved ultraviolet protection effects and also has excellent resistance to sweat or water is obtainable by incorporating ultraviolet protection powders in both the outer oil phase and inner oil phase of the composition, thereby uniformly distributing the ultraviolet protection agent on the skin during its application.

The cosmetic composition according to the present invention has high ultraviolet protection effects and also has excellent water resistance when applied to the skin.

The cosmetic composition of the present invention is an $O_1/W/O_2$ emulsion composition and containing, in both an inner oil phase $O_1$ and an outer oil phase $O_2$ thereof, fine metal oxide particles having ultraviolet screening ability.

As the fine metal oxide particles to be incorporated in the oil phases $O_1$ and $O_2$ and having ultraviolet screening ability, zinc oxide, titanium oxide and cerium oxide are preferred because they are metal oxides having the effects of absorbing or scattering a wide range of UV rays from UVB to UVAII and are highly effective for absorbing or scattering ultraviolet light. These fine metal oxide particles each have an average particle size of preferably from 0.001 to 0.5 µm, more preferably from 0.01 to 0.1 µm.

Examples of the commercially available fine metal oxide particles include fine zinc oxide particles such as "FINEX-25", "FINEX-50", and "FINEX-75" (each, product of Sakai Chemical Industry), "MZ500 Series" and "MZ700 Series" (each, product of Tayca Corporation), and "ZnO-350" (product of Sumitomo Osaka Cement); fine titanium oxide particles such as "TTO-55 Series" and "TTO-51 Series" (each, product of Ishihara Sangyo Kaisha), and "JR series" and "JA series" (each, product of Tayca Corporation); and fine cerium oxide particles such as high-purity cerium oxide sold by Nikki and Seimi Chemical. Of these, zinc oxide and titanium oxide are preferred.

In the invention, the fine metal oxide particles having ultraviolet screening ability are preferably under a dispersible state in the dispersion. To facilitate dispersion, the surface of the fine metal oxide particles may be covered with another substance, or the inorganic substance particles may be mixed with a dispersing assistant sol, for example, $Al_2O_3$ sol or a stabilizer of a sol. When ultrafine titanium oxide particles are employed, for example, dispersion stability can be heightened by covering the surface of the ultrafine particles with at least one oxide or hydrous oxide of an element selected from Al, Si, Zr, Mg, Zn, Ce, Ti and Fe.

The surface of the fine metal oxide particles is preferably subjected to hydrophobic treatment which is ordinarily given to powders for cosmetic compositions in order to improve resistance to sweat or water (hydrophobic ultraviolet protection powder).

No limitation is imposed on the surface treatment method insofar as it improves water repellency of the metal oxide. Examples of the method include treatment with silicone such as methyl hydrogen polysiloxane, dimethylpolysiloxane or silicone resin or treatment with a fluorine compound such as a perfluoro-containing compound. Of these, the metal oxide subjected to silicone treatment is preferred.

For the incorporation (dispersion) of the fine metal oxide particles in the oil phase $O_1$, use of (b) a polymer composed of a hydrophobic monomer unit and a hydrophilic monomer unit and containing the hydrophilic monomer unit preferably in an amount of from 40 to 80 wt. %, more preferably from 40 to 60 wt. % is preferred.

As such a polymer, nonionic or cationic polymers are preferred; the polymers in which a hydrophobic monomer unit and a hydrophilic monomer unit have been each polymerized to form a macromer are more preferred; and the polymers in which the hydrophobic macromer has a siloxane skeleton are even more preferred. Examples include polymers having a siloxane chain as a skeleton (hydrophobic macromer) and having, added thereto, a hydrophilic macromer such as a polyoxyalkylene group such as polyoxyethylene or polyoxypropylene, an oxazoline group or an amino group. Specific examples include polyoxyethylene.methylpolysiloxane copolymer, poly(oxyethylene.oxypropylene)methylpolysiloxane copolymer, (polyoxyethylene alkylpolysiloxane).(polyoxypropylene alkylpolysiloxane).dimethylpolysiloxane copolymer, methylpolysiloxane.(alkyl methylpolysiloxane).{poly(oxyethylene-oxypropylene)methylpolysiloxane}copolymer, amino-modified silicone and oxazoline-modified silicone.

Of these, oxazoline-modified silicone (poly-N-acylethyleneimine-modified silicone) as described in JP-A-7-133352 is preferred.

The polymer has a molecular weight preferably ranging from 10000 to 250000, more preferably from 10000 to 200000.

As the oil phase $O_1$, oil components used for ordinary cosmetic compositions can be employed and the oil phase containing silicone oil is preferred. The oil phase $O_1$ is preferably a dispersion containing the following components (a), (b), (c) and (d):

(a) fine metal oxide particles having ultraviolet screening ability,
(b) a polymer composed of a hydrophobic monomer unit and a hydrophilic monomer unit,
(c) a silicone oil, and
(d) an alcohol having from 1 to 3 carbon atoms at an (a):(b):(c):(d) weight ratio of (from 25 to 65):(from 0.1 to 5):(from 10 to 50):(from 10 to 50); more preferably (from 25 to 65):(from 0.5 to 4):(from 20 to 50):(from 10 to 50). Within the above-described range, a stable dispersion can be obtained.

Although no particular limitation is imposed on the silicone oil (c) insofar as it is in the liquid form at 20° C. and can disperse therein the ultraviolet protection powders (a), examples include dimethylpolysiloxane and methylcyclopolysiloxane. The silicone oil having a viscosity at 20° C. of from 1 to 1000 mm²/s is preferred from the viewpoint of the feel to the touch.

Examples of the alcohol (d) having from 1 to 3 carbon atoms include methanol, ethanol and propanol, of which ethanol is preferred. A mixture of them may also be usable.

To improve the dispersibility of the powders, use of the alcohol (d) having from 1 to 3 carbon atoms in an amount of from 0.5 to 5 times the weight of the silicone oil (c) is preferred.

As well as the components (a), (b), (c) and (d), powders, oil components, ultraviolet absorbers other than the above-descried ones can be added to the oil phase $O_1$.

The $O_1/W/O_2$ emulsion composition of the present invention can be obtained, for example, by preparing an $O_1/W$ emulsion containing, in an oil phase $O_1$ thereof, fine metal oxide particles having ultraviolet screening ability by means of a polymer (A) composed of a hydrophobic monomer unit and a hydrophilic monomer unit and containing the hydrophilic monomer unit in an amount of from 40 to 80 wt. %; and then emulsifying the resulting $O_1/W$ emulsion in an oil phase $O_2$ containing fine metal oxide particles having ultraviolet screening ability by means of an emulsifier (B).

Examples of the polymer as Component (A) are similar to those of component (b).

The polymer as Component (A) and the Polymer (b) may be the same or different, but they are preferably the same.

The oil phase $O_1$ is contained in the entire composition preferably in an amount of from 1 to 40 wt. %, more preferably from 5 to 30 wt. %.

The water phase W is contained in the entire composition preferably in an amount of from 5 to 60 wt. %, more preferably from 10 to 50 wt. %.

The polymer (A) is used for emulsifying the oil phase $O_1$ containing the fine metal oxide particles having ultraviolet screening ability and the water phase W and it is contained preferably in an amount of from 0.05 to 5 wt. %, more preferably from 0.2 to 5 wt. % in the entire composition.

The average particle size of the oil phase $O_1$ in the water phase W is preferably as small as possible because if so, dispersion resulting from Brownian motion becomes stable. The average particle size is preferably 10 µm or less, more preferably 1 µm or less. The average particle size of the $O_1$ of $O_1/W$ is measured by a laser scattering particle size distribution analyzer. The particle size of the $O_1$, in the $O_1/W/O_2$ emulsion cosmetic composition is determined from an optical microscope image.

The $O_1/W/O_2$ emulsion cosmetic composition of the present invention is available by emulsifying the resulting $O_1/W$ emulsion in the oil phase $O_2$ containing the fine metal oxide particles having ultraviolet screening ability by means of the emulsifier (B).

As the emulsifier (B), a highly oil-soluble W/O emulsifier is preferred. For example, a nonionic emulsifier having an HLB of 7 or less can be used. Specific examples include silicone surfactants such as polyether modified silicones, glyceryl alkyl modified silicones, polyoxyethylene alkyl ethers, sorbitan fatty acid esters, polyoxyethylene sorbitan fatty acid esters, polyoxyethylene fatty acid esters, polyoxyethylene fatty acid esters, polyoxyethylene hydrogenated castor oil, polyoxyethylene hydrogenated castor oil fatty acid esters, polyglycerin fatty acid esters, polyoxyethylene glyceryl ether fatty acid esters, polyoxyethylene fatty acid monoalkanolamides, polyoxyethylene fatty acid dialkanolamides and sucrose fatty acid esters.

As the emulsifier (B), polymers composed of a hydrophobic monomer unit and a hydrophilic monomer unit and containing from 5 to 50 wt. %, preferably from 10 to 40 wt. %, of the hydrophilic monomer unit are usable.

Such polymers are similar to those described above in the polymer (b) and Polymer (A) except for the content of the hydrophilic monomer unit.

One or more of these emulsions can be used as Component (B) and its content is preferably from 0.01 to 10 wt. % in the entire composition.

The oil component contained in the oil phase $O_2$ is, for example, a silicone oil, hydrocarbon oil, ester oil, ether oil or fluorinated oil.

Examples of the silicone oil include linear polyorganosiloxanes and cyclic polysiloxanes. The linear polyorganosiloxanes include linear alkylpolysiloxanes having an alkyl group with 1 to 5 carbon atoms, and linear alkylarylpolysiloxanes having an alkyl group with 1 to 5 carbon atoms and an aryl group with 6 to 10 carbon atoms. Specific examples include linear dimethylpolysiloxane and linear methylphenylpolysiloxane. Of these linear organopolysiloxanes, those having a viscosity at 20° C. of from 1 to 1000 mPa·s are preferred, with those having a viscosity at 20° C. of from 5 to 10 mPa·s being more preferred. The cyclic polysiloxanes include 4- to 6-membered cyclic siloxanes having, as a substituent, an alkyl group with 1 to 5 carbon atoms. Specific examples include octamethylcyclotetrasiloxane and decamethylcyclopentasiloxane.

Examples of the hydrocarbon oil include liquid paraffin, squalane, light liquid isoparaffin, heavy liquid isoparaffin and polybutene.

Examples of the ester oil include plant oils such as safflower oil, soybean oil, grapeseed oil, perilla oil, wheat germ oil, avocado oil, olive oil, castor oil, Macadamia nut oil, and meadowfoam oil; animal oils such as mink oil, turtle oil and liquid lanoline; fatty acid esters of a lower alcohol such as isopropyl myristate, isopropyl isostearate and isopropyl lanolate; fatty acid ester of a higher alcohol such as 2-ethylhexyl isononanoate, isotridecyl isononanoate, octyldodecyl myristate, octyldodecyl oleate, cetyl 2-ethylhexanoate, isocetyl 2-ethylhexanoate, and isostearyl isostearate; oxyacid esters of a higher alcohol such as diisostearyl malate and cetyl lactate; and fatty acid esters of a polyol such as glyceryl tricaprylate, glyceryl tri-2-ethylhexanoate, glyceryl triisostearate, glyceryl(tricaprylate.caprate), propylene glycol dicaprylate, propylene glycol di(caprylate.caprate), propylene glycol diisostearate, neopentyl glycol dicaprate, and neopentyl glycol 2-ethylhexanoate.

Examples of the ether oil include cetyl dimethyl butyl ether, while those of the fluorinated oil include perfluoropolyether and perfluorocarbon.

Of these, silicone oils are preferred.

The oil phase $O_2$ is contained in the entire composition preferably in an amount of from 30 to 90 wt. %, more preferably from 40 to 80 wt. %.

To the oil phase $O_2$, dextrin palmitate or alkyl-modified silicone may be added in order to improve the stability. Its content in the oil phase $O_2$ is preferably from 0.001 to 3 wt. %, more preferably from 0.01 to 2 wt. %, even more preferably from 0.1 to 1 wt. %.

The fine metal oxide particles to be dispersed in the oil phase $O_1$ and the fine metal oxide particles to be dispersed in the oil phase $O_2$ are adjusted preferably to a (particles in $O_1$/particles in $O_2$) weight ratio of from 1:9 to 9:1, more preferably from 2:8 to 7:3. Weight ratios within the above-described range enable more uniform incorporation of the particles and production of higher ultraviolet protection effects.

The cosmetic composition of the present invention can contain an organic ultraviolet absorber further for improving the ultraviolet protection effects. No particular limitation is imposed on the organic ultraviolet absorber, but an oil soluble one is preferred.

The oil soluble ultraviolet absorbers include benzoic acid, anthranilic acid, salicylic acid, cinnamic acid and benzophenone ultraviolet absorbers. Examples of the benzoic acid ultraviolet absorber include para-aminobenzoic acid (which will hereinafter be abbreviated as PABA), glyceryl PABA, ethyl dihydroxypropyl PABA, N-ethoxylate PABA ethyl ester, N-dimethyl PABA ethyl ester, N-dimethyl PABA butyl ester, N-dimethyl PABA amino ester and octyldimethyl PABA. Those of the anthranilic acid one include homomethyl-N-acetyl anthranilate. Those of the salicylic acid one include amyl salicylate, menthyl salicylate, homomethyl salicylate, octyl salicylate, phenyl salicylate, benzyl salicylate and p-isopropanolphenyl salicylate. Those of the cinnamic acid one include octyl cinnamate, ethyl-4-isopropyl cinnamate, ethyl-2,4-diisopropyl cinnamate, methyl-2,4-diisopropyl cinnamate, propyl p-methoxycinnamate, isopropyl p-methoxycinnamate, isoamyl p-methoxycinnamate, 2-ethylhexyl p-methoxycinnamate, 2-ethoxyethyl p-methoxycinnamate, cyclohexyl p-methoxycinnamate, ethyl α-cyano-β-phenyl-cinnamate, 2-ethylhexyl α-cyano-β-phenylcinnamate and glyceryl mono-2-ethylhexanoyl di-para-methoxycinnamate. Those of the benzophenone one include 2,4-dihydroxybenzophenone, 2,2'-dihydroxy-4-methoxy-benzophenone, 2,2'-dihydroxy-4,4'-dihydroxybenzophenone, 2-hydroxy-4-methoxybenzophenone, 2-hydroxy-4-methoxy-4'-methylbenzophenone, 2-hydroxy-4-methoxybenzophenone, 4-phenylbenzophenone, 2-ethylhexyl-4'-phenylbenzophenone-2-carboxylate, 2-hydroxy-4-n-octoxybenzophenone and 4-hydroxy-3-carboxybenzophenone. Additional examples include 3-(4'-methylbenzylidene)-dl-camphor, 3-benzylidene-dl-camphor, ethyl urocanate, 2-phenyl-5-methylbenzoxazole, 2,2'-hydroxy-5-methylphenylbenzotriazole, 2-(2'-hydroxy-5-t-octylphenyl) benzotriazole, dibenzalazine, dianisoylmethane, 4-methoxy-4'-t-butyl-benzoylmethane, 5-(3,3-dimethyl-2-norbornylidene)-3-pentan-2-one, benzene bis-1,3-diketone derivatives as described in JP-A-2-212579 and benzoylpinacolone derivatives as described in JP-A-3-220153.

The content of the organic ultraviolet absorber in the cosmetic composition is not limited, but is preferably from 0.1 to 25 wt. %, more preferably from 0.5 to 10 wt. % in the entire composition in order to heighten the ultraviolet protection effects and provide a good feeling upon use.

These organic ultraviolet absorbers may be added to the oil phase $O_1$ and/or the oil phase $O_2$.

The cosmetic composition of the present invention may further contain a skin whitening agent or a plant extract having skin whitening effects. As the skin whitener, ascorbic acids, hydroquinones, kojic acids, and placenta extract can be used. Examples of the ascorbic acids include L-ascorbic acid, L-ascorbic acid glucoside, and alkali metal salts of phosphate ester of L-ascorbic acid. Examples of the hydroquinones include condensates between saccharide and an alkylhydroquinone obtained by introducing an alkyl group having from 1 to 4 carbon atoms into hydroquinone. Examples of the kojic acids include kojic acid, kojic acid monobutylate, kojic acid fatty acid ester. Examples of the placenta extract include placenta extract.

Examples of the plant extracts having skin whitening effects include extracts of licorice, Puerariae *Radix*, black bean, *Amana edulis*, Anemarrhena, dowarf lilyturf, *Sansevieria*, *Quercus salicina*, Artemisiae *Capillari* Flos., chamomile (oil soluble and water soluble ones), *sanguisorba officinalis* extract, artichoke, aster, rice, clove, turmeric, balsam pear, Dioscorea *Rhizome*, aloe, tea, meadow saxifrage, Scutellariae *Radix*, Japanese loquat, bitter orange, panax ginseng, althea, cinchona, comfrey, rosemary, scopolia, *Sargassum fulvellum*, burnet, and blueberry.

Of these whiteners, oil soluble chamomile extract, *sanguisorba officinalis* extract, tea extract, Puerariae *Radix* extract, licorice extract, althea extract, burnet extract, clove extract, L-ascorbic acid, L-ascorbic acid glucoside, kojic acid and placenta extract are preferred, with oil soluble chamomile extract and *sanguisorba officinalis* extract being especially preferred because they have high skin-color improving effects. These extracts are incorporated in the cosmetic composition of the present invention in an amount of from 0.001 to 5 wt. %.

The cosmetic composition of the present invention may further contain components ordinarily employed for cosmetic compositions such as liquid oils, solid fats (waxes), semisolid oils, alcohols, water, humectants, water soluble polymers, oil soluble polymers, polymer latexes, various surfactants, drugs, plant extracts, ceramides, blood circulation accelerators, cooling agents, antiperspirants, bactericides, skin activators, pH regulators, thickeners, antioxidants, antiseptics, and perfumes.

The cosmetic composition of the present invention can be used as various cosmetic compositions imparted with ultraviolet protection properties, for example, skin care cosmetic compositions, makeup cosmetic compositions and hair cosmetic compositions. As the makeup cosmetic compositions, they are suited as sunscreen cosmetic compositions, foundations, face powders, makeup bases, cheek rouge, lip rouge, concealer and eye cosmetics.

EXAMPLES

Preparation Example 1

Preparation of Oxazoline-Modified Silicone)

In 140 g of dehydrated ethyl acetate were dissolved 3.76 g (0.024 mol) of diethyl sulfate and 65.3 g (0.66 mol) of 2-ethyl-2-oxazoline. Under a nitrogen atmosphere, the resulting solution was heated under reflux for 8 hours to synthesize terminal-reactive poly(N-propionylethyleneimine). To the resulting product was added, in one portion, a 50% ethyl acetate solution of 500 g (0.024 mol in terms of an amino group) of a side-chain primary aminopropyl-modified polydimethylsiloxane (molecular weight: 100000, amine equivalent: 20500), followed by heating under reflux for 12 hours. The reaction mixture was concentrated under reduced pressure to yield an N-propionylethyleneimine-dimethylsiloxane copolymer as a pale yellow rubbery solid (537 g, yield: 95%). The copolymer had a weight average molecular weight of 149000 (hydrophilic macromer content: 12 wt. %).

Preparation Example 2

Preparation of Oxazoline-Modified Silicone

In 550 g of dehydrated ethyl acetate were dissolved 7.57 g (0.049 mol) of diethyl sulfate and 263.3 g (2.66 mol) of 2-ethyl-2-oxazoline. Under a nitrogen atmosphere, the resulting solution was heated under reflux for 8 hours to synthesize terminal reactive poly(N-propionylethyleneimine). To the resulting product was added, in one portion, a 50% ethyl acetate solution of 250 g (0.065 mol in terms of an amino group) of a side-chain primary aminopropyl-modified polydimethylsiloxane (molecular weight: 60000, amine equivalent: 3870), followed by heating under reflux for 12 hours. The reaction mixture was concentrated under reduced pressure to yield an N-propionylethyleneimine-dimethylsiloxane copolymer as a pale yellow rubbery solid (505 g, yield: 97%). The copolymer had a weight average molecular weight of 88400 (hydrophilic macromer content: 49 wt. %).

Examples 1 and 2, Comparative Examples 1 to 4

Liquid ultraviolet protection cosmetic compositions were each prepared in accordance with the composition in Table 1 and they were evaluated for ultraviolet protection effects and water resistance. The results are shown collectively in Table 1.

(Preparation Process)

(1) Examples 1 and 2

Phase IV was obtained by uniformly mixing Components (13), (14) and (17) and dispersing Component (15) in the resulting uniform mixture. Phase I was obtained by dispersing Component (1) in a uniform mixture of Components (4) to (6). Phase II was obtained by mixing Component (7) with Component (8), followed by homogenization. Phase II was added to Phase I and the resulting mixture was homogenized. After the addition of Components (9), (10) and (12) thereto and homogenization, the resulting mixture was added to Phase IV, followed by homogenization, whereby a cosmetic composition ($O_1/W/O_2$ emulsion) was obtained.

(2) Comparative Example 1

A cosmetic composition was obtained by dispersing Component (15) in a mixture of Components (13), (14) and (17) to obtain Phase IV, mixing Components (9), (10) and (12), adding the resulting mixture to Phase IV and then homogenizing the mixture.

(3) Comparative Examples 2 and 3

Cosmetic compositions were each obtained by dispersing Component (15) or (16) in a mixture of Components (13), (14) and (17) to obtain Phase IV, mixing Component (2) or (3) with Components (9), (10) and (12), adding the resulting mixture to Phase IV and homogenizing the mixture.

(4) Comparative Example 4

A cosmetic composition was obtained by uniformly mixing Components (13), (14) and (17) to obtain Phase IV, mixing Components (9) to (12), adding the resulting mixture to Phase IV and then homogenizing the mixture.

(Evaluation Method)
(1) Ultraviolet Protection Effects:

The SPF value of each cosmetic composition was measured using an SPF analyzer (product of Optometrics) and evaluated in accordance with the following criteria.

A: SPF of 20 or greater.
B: SPF of 15 or greater but less than 20.
C: SPF of 5 or greater but less than 15.
D: SPF less than 5.
(2) Water Resistance (SPF Value after Water Treatment):

A surgical tape was adhered to a quartz plate. Each cosmetic composition was applied onto the tape (coating weight: 2 mg/cm$^2$) and SPF value was measured using an SPF analyzer (product of Optometrics). After treatment in water for 80 minutes, the SPF value was measured again and (SPF value after water treatment)/(SPF value before water treatment)×100(%) was calculated. The stability (sustainability) of the SPF value was judged in accordance with the below-described criteria and used as an indicator of water resistance.
A (extremely high water resistance): 90% or greater
B (high water resistance): 70% or greater but less than 90%
C (low water resistance): less than 70%.

cosmetic composition of Comparative Example 2 having hydrophilic ultraviolet protection powders dispersed in an oil phase O thereof had low ultraviolet protection effects and water resistance. Similarly, the cosmetic composition of Comparative Example 3 having hydrophilic titanium oxide dispersed in the oil phase O thereof had low water resistance. The cosmetic composition of Comparative Example 4 having a water soluble ultraviolet absorber (phenylbenzimidazole sulfonic acid) incorporated in the water phase thereof did not have sufficient water resistance.

Examples 3 to 5, Comparative Examples 5 and 6

Liquid ultraviolet protection cosmetic compositions were prepared in accordance with the composition as shown in Table 2 and as in Example 1, they were evaluated for ultraviolet protection effects (SPF value). The results are shown collectively in Table 2.

TABLE 1

| | | | Examples | | Comparative Examples | | | |
|---|---|---|---|---|---|---|---|---|
| | Components (wt. %) | | 1 | 2 | 1 | 2 | 3 | 4 |
| Phase I | 1 | Silicone-covered fine zinc oxide particles *1 | 5.0 | 5.0 | | | | |
| | 2 | Untreated zinc oxide | | | | 5.0 | | |
| | 3 | Untreated titanium oxide | | | | | 5.0 | |
| | 4 | Methylcyclopolysiloxane *2 | 10.0 | 6.4 | | | | |
| | 5 | Oxazoline-modified silicone (Prep. Ex. 1) | | 0.6 | | | | |
| | 6 | Ethanol | | 5.9 | | | | |
| Phase II | 7 | Oxazoline-modified silicone (Prep. Ex. 2) | 2.1 | 2.1 | | | | |
| | 8 | Ethanol | 5.0 | 5.0 | | | | |
| Phase III | 9 | Ethanol | 10.0 | 10.0 | 10.0 | 10.0 | 10.0 | 10.0 |
| | 10 | Glycerin | 3.0 | 3.0 | 3.0 | 3.0 | 3.0 | 5.0 |
| | 11 | Phenylbenzimidazole sulfonic cid | | | | | | 3.0 |
| | 12 | Purified water | Balance | Balance | Balance | Balance | Balance | Balance |
| Phase IV | 13 | Polyoxyethylene-methylpolysiloxane copolymer *3 | 1.2 | 1.2 | 1.2 | 1.2 | 1.2 | 1.2 |
| | 14 | 2-Ethylhexyl paramethoxycinnamate | 3.0 | 3.0 | 3.0 | 3.0 | 3.0 | 5.0 |
| | 15 | Silicone-covered fine zinc oxide particles *1 | 5.0 | 5.0 | 10.0 | 5.0 | | |
| | 16 | Silicone-covered fine titanium oxide particles *4 | | | | | 5.0 | |
| | 17 | Methylcyclopolysiloxane | 25.7 | 22.8 | 42.8 | 42.8 | 42.8 | 45.8 |
| | | Total | 100 | 100 | 100 | 100 | 100 | 100 |
| Evaluation | | Ultraviolet protection effects | B | A | C | C | B | C |
| | | Water resistance | B | B | B | C | D | C |

*1: obtained by covering fine zinc oxide particles ("ZnO-350", product of Sumitomo Osaka Cement) with 6 wt. % (corresponding to 1.3 mg/m$^2$) of methyl hydrogen polysiloxane
*2: "SH245" (product of Dow Corning Toray Silicone)
*3: "Silicone SH3775M" (product of Dow Corning Toray Silicone), content of a hydrophilic monomer unit: 25 wt. %.
*4: obtained by covering fine titanium oxide particles ("TTO-51A", product of Ishihara Sangyo Kaisha) with 8 wt. % (corresponding to 1.0 mg/m$^2$) of methyl hydrogen polysiloxane.

The cosmetic compositions ($O_1/W/O_2$ emulsion) obtained in Examples 1 and 2 had high ultraviolet protection effects, excellent water resistance and long-lasting ultraviolet protection effects. The cosmetic composition obtained in Example 2 was superior in dispersion stability of the ultraviolet protection agent (metal oxide) dispersed in Phase I and its ultraviolet protection effects were very high.

The cosmetic compositions obtained in Comparative Examples 1 to 4, on the other hand, are W/O emulsion cosmetic compositions. The cosmetic composition of Comparative Example 1 containing hydrophobic ultraviolet protection powders only in the oil phase O thereof had low ultraviolet protection effects and was inferior in feeling upon use. The (Preparation Process)

Phase IV was obtained by dispersing Components (11) and (12) in a mixture of Components (13) to (16), adding the resulting dispersion to Component (10), and mixing the resulting mixture uniformly. Phase I was then obtained by dispersing Components (1) and (2) in a uniform mixture of Components (3) to (5). Component (6) was mixed with Component (7), and Phase II thus obtained was added to Phase I, followed by homogenization. By adding Components (8) and (9) to the uniform mixture, uniform $O_1$/W emulsion was obtained. The resulting O/W emulsion was added to Phase IV, followed by homogenization, whereby an $O_1/W/O_2$ cosmetic composition was obtained.

TABLE 2

|  |  | Components (wt. %) | Examples 3 | Examples 4 | Examples 5 | Comp. Ex. 5 | Comp. Ex. 6 |
|---|---|---|---|---|---|---|---|
| Phase I | 1 | Silicone-covered fine zinc oxide particles *1 | 1.0 | 1.9 | 2.9 |  | 3.9 |
|  | 2 | Silicone-covered fine titanium oxide particles *4 | 0.2 | 0.3 | 0.5 |  | 0.6 |
|  | 3 | Oxazoline-modified silicone (Prep. Ex. 1) | 0.1 | 0.3 | 0.4 |  | 0.6 |
|  | 4 | Methylcyclopolysiloxane *2 | 1.4 | 2.8 | 4.3 |  | 5.7 |
|  | 5 | Ethanol | 1.3 | 2.6 | 3.9 |  | 5.3 |
| Phase II | 6 | Oxazoline-modified silicone (Prep. Ex. 2) | 0.1 | 0.3 | 0.4 |  | 0.6 |
|  | 7 | Ethanol | 0.3 | 0.7 | 1.0 |  | 1.3 |
| Phase III | 8 | Ethanol | 5.5 | 5.5 | 5.5 | 5.5 | 5.5 |
|  | 9 | Purified water | Balance | Balance | Balance | Balance | Balance |
| Phase IV | 10 | Polyoxyethylene-methylpolysiloxane copolymer *3 | 1.2 | 1.2 | 1.2 | 1.2 | 1.2 |
|  | 11 | Silicone-covered fine zinc oxide particles *1 | 2.8 | 2.0 | 0.9 | 3.9 |  |
|  | 12 | Silicone-modified fine titanium oxide particles *4 | 0.5 | 0.3 | 0.2 | 0.6 |  |
|  | 13 | Oxazoline-modified silicone (Prep. Ex. 1) | 0.4 | 0.3 | 0.1 | 0.6 |  |
|  | 14 | Methylcyclopolysiloxane *2 | 4.3 | 2.8 | 1.4 | 5.7 |  |
|  | 15 | Ethanol | 3.9 | 2.6 | 1.3 | 5.3 |  |
|  | 16 | Methylpolysiloxane | 50.0 | 50.0 | 50.0 | 50.0 | 50.0 |
|  |  | Total | 100 | 100 | 100 | 100 | 100 |
| Ultraviolet protection effects (SPF value) |  |  | 7.2 | 8.5 | 6.3 | 5.5 | 5.0 |

The cosmetic compositions obtained in Examples 3 to 5 each had high ultraviolet protection effects. Of these cosmetic compositions having water soluble components and oil soluble components at a weight ratio of about 4:6, the cosmetic composition of Example 4 having hydrophobic protection powders in the inner oil phase and in the outer oil phase at a ratio of 5:5, close to 4:6, had the highest ultraviolet protection effects. On the contrary, the cosmetic compositions obtained in Comparative Examples 5 and 6 having hydrophobic ultraviolet protection powders only in the outer oil phase or only in the inner phase thereof were inferior in the ultraviolet protection effects.

Example 6

Sunscreen Lotion

A sunscreen lotion having the below-described composition was prepared in a similar manner to that employed in Example 1.
(Composition)

|  | (wt. %) |
|---|---|
| Phase I |  |
| (1) Silicone-covered zinc oxide | 3.8 |
| (2) Silicone-covered titanium oxide | 0.6 |
| (3) Oxazoline-modified silicone (Prep. Ex. 2) | 0.3 |
| (4) Methylcyclopolysiloxane | 3.8 |
| (5) Ethanol | 2.6 |
| Phase II |  |
| (6) Oxazoline-modified silicone (Prep. Ex. 2) | 0.8 |
| (7) Ethanol | 1.9 |
| Phase III |  |
| (8) Ethanol | 2.9 |
| (9) Water | Balance |
| (10) Glycerin | 3.5 |
| Phase IV |  |
| (11) Polyoxyethylene•methylpolysiloxane copolymer | 0.8 |
| (12) Silicone-covered zinc oxide | 11.0 |
| (13) Silicone-covered titanium oxide | 0.2 |

-continued

|  | (wt. %) |
|---|---|
| (14) Methylsiloxane network polymer | 5.0 |
| (15) Methylcyclopolysiloxane | 20.0 |
| (16) Dimethylpolysiloxane | 15.0 |
| (17) 2-Ethylhexyl paramethoxycinnamate | 4.0 |
| (18) Oil-soluble chamomile extract | 0.5 |

As a result of observation by an optical microscope, the particle size of $O_1$ of the $O_1/W/O_2$ sunscreen lotion thus obtained was 5 μm or less and the Brownian motion of the particles was confirmed.

Example 7

Sunscreen Lotion

A sunscreen lotion having the below-described composition was prepared in a similar manner to that employed in Example 1.
(Composition)

|  | (wt %) |
|---|---|
| Phase I |  |
| (1) Silicone-covered zinc oxide | 10.5 |
| (2) Silicone-covered titanium oxide | 1.7 |
| (3) Oxazoline-modified silicone (Prep. Ex. 2) | 0.9 |
| (4) Methylcyclopolysiloxane | 10.5 |
| (5) Ethanol | 7.0 |
| Phase II |  |
| (6) Oxazoline-modified silicone (Prep. Ex. 2) | 2.2 |
| (7) Ethanol | 5.2 |
| Phase III |  |
| (8) Ethanol | 7.8 |
| (9) Water | Balance |
| (10) Glycerin | 9.5 |
| Phase IV |  |
| (11) Polyoxyethylene•methylpolysiloxane copolymer | 0.5 |
| (12) Silicone-covered zinc oxide | 1.4 |

-continued

| | (wt %) |
|---|---|
| (13) Silicone-covered titanium oxide | 0.1 |
| (14) Methylsiloxane network polymer | 5.0 |
| (15) Methylcyclopolysiloxane | 2.0 |
| (16) Dimethylpolysiloxane | 25.6 |
| (17) 2-Ethylhexyl paramethoxycinnamate | 4.0 |

Example 8

Sunscreen Lotion

A sunscreen lotion having the below-described composition was prepared in a similar manner to that employed in Example 1.
(Composition)

| | (wt. %) |
|---|---|
| Phase I | |
| (1) Silicone-covered zinc oxide | 1.0 |
| (2) Silicone-covered titanium oxide | 0.2 |
| (3) Oxazoline-modified silicone (Prep. Ex. 2) | 0.1 |
| (4) Methylcyclopolysiloxane | 1.0 |
| (5) Ethanol | 0.6 |
| Phase II | |
| (6) Oxazoline-modified silicone (Prep. Ex. 2) | 2.1 |
| (7) Ethanol | 0.5 |
| Phase III | |
| (8) Ethanol | 0.7 |
| (9) Water | Balance |
| (10) Glycerin | 0.9 |
| Phase IV | |
| (11) Polyoxyethylene•methylpolysiloxane copolymer | 0.3 |
| (12) Silicone-covered zinc oxide | 4.4 |
| (13) Silicone-covered titanium oxide | 0.1 |
| (14) Methylsiloxane network polymer | 5.0 |
| (15) Methylcyclopolysiloxane | 2.0 |
| (16) Dimethylpolysiloxane | 78.5 |
| (17) 2-Ethylhexyl paramethoxycinnamate | 4.0 |

Example 9

Sunscreen Cream

A sunscreen cream having the below-described composition was prepared in a similar manner to that employed in Example 1.
(Composition)

| | (wt. %) |
|---|---|
| Phase I | |
| (1) Silicone-covered zinc oxide | 3.8 |
| (2) Silicone-covered titanium oxide | 0.6 |
| (3) Oxazoline-modified silicone (Prep. Ex. 2) | 0.3 |
| (4) Methylcyclopolysiloxane | 3.8 |
| (5) Ethanol | 2.6 |
| Phase II | |
| (6) Oxazoline-modified silicone (Prep. Ex. 2) | 0.8 |
| (7) Ethanol | 1.9 |

-continued

| | (wt. %) |
|---|---|
| Phase III | |
| (8) Ethanol | 2.9 |
| (9) Water | Balance |
| (10) Magnesium sulfate | 1.0 |
| (11) Glycerin | 7.0 |
| Phase IV | |
| (12) Polyoxyethylene•methylpolysiloxane copolymer | 2.0 |
| (13) Silicone-covered zinc oxide | 11.0 |
| (14) Silicone-covered titanium oxide | 0.2 |
| (15) Methylsiloxane network polymer | 3.0 |
| (16) Methylcyclopolysiloxane | 20.0 |
| (17) Dimethylpolysiloxane | 15.0 |
| (18) 2-Ethylhexyl paramethoxycinnamate | 3.0 |
| (19) Squalane | 2.0 |
| (20) Dextrin palmitate | 0.5 |

Example 10

Sunscreen Foundation

A sunscreen foundation having the below-described composition was prepared in a similar manner to that employed in Example 1.
(Composition)

| | (wt. %) |
|---|---|
| Phase I | |
| (1) Silicone-covered zinc oxide | 3.8 |
| (2) Silicone-covered titanium oxide | 0.6 |
| (3) Oxazoline-modified silicone (Prep. Ex. 2) | 0.3 |
| (4) Methylcyclopolysiloxane | 3.8 |
| (5) Ethanol | 2.6 |
| Phase II | |
| (6) Oxazoline-modified silicone (Prep. Ex. 2) | 0.8 |
| (7) Ethanol | 1.9 |
| Phase III | |
| (8) Ethanol | 2.9 |
| (9) Water | Balance |
| (10) Glycerin | 3.5 |
| Phase IV | |
| (11) Polyoxyethylene•methylpolysiloxane copolymer | 0.8 |
| (12) Silicone-covered zinc oxide | 11.0 |
| (13) Silicone-covered titanium oxide | 0.2 |
| (14) Methylsiloxane network polymer | 5.0 |
| (15) Coloring pigment | q.s. |
| (16) Methylcyclopolysiloxane | 20.0 |
| (17) Dimethylpolysiloxane | 15.0 |
| (18) 2-Ethylhexyl paramethoxycinnamate | 4.0 |
| (18) Perfume | trace |

The cosmetic compositions obtained in Examples 6 to were evaluated for their ultraviolet protection effects and water resistance as in Example 1. As a result, each composition had high ultraviolet protection effects and excellent water resistance.

The invention claimed is:
1. A process for preparing a cosmetic composition, wherein said cosmetic composition comprises:
an $O_1/W/O_2$ emulsion composition, which comprises, in oil phases $O_1$ and $O_2$ thereof, fine metal oxide particles having ultraviolet screening ability, and wherein said process comprises:
(a) preparing an $O_1$/W emulsion comprising, in the oil phase $O_1$ thereof, fine metal oxide particles having ultraviolet screening ability, by means of (A) a polymer composed of hydrophobic monomer units and hydrophilic monomer units and containing said hydrophilic monomer units in an amount of from 40 to 80 wt. %; and
(b) emulsifying said $O_1$/W emulsion in an oil phase $O_2$, comprising fine metal oxide particles having ultraviolet screening ability, with (B) an emulsifier,
wherein said emulsifier (B) is at least one of macromer selected from the group consisting of a oxazoline-modified silicone and a polyoxyethylene methylpolysiloxane copolymer, wherein the oxazoline unit and the polyoxyethylene unit are present in the respective macromer in an amount of from 5 to 50 wt. %.

2. The process according to claim 1, wherein a weight ratio of said fine metal oxide particles dispersed in the oil phase $O_1$ to said fine metal oxide particles dispersed in the oil phase $O_2$ falls within a range of from 1:9 to 9:1.

3. The process according to claim 1, wherein said fine metal oxide particles having ultraviolet screening ability have been treated with a silicone and said oil phases $O_1$ and $O_2$ each contain a silicone oil.

4. The process according to claim 2, wherein said fine metal oxide particles having ultraviolet screening ability have been treated with a silicone and the oil phases $O_1$ and $O_2$ each contain a silicone oil.

5. The process according to claim 1, wherein said oil phase $O_1$ is a dispersion comprising:
(a) fine metal oxide particles having ultraviolet screening ability;
(b) a polymer containing a hydrophobic monomer unit and a hydrophilic monomer unit;
(c) a silicone oil; and
(d) an alcohol having from 1 to 3 carbon atoms,
wherein said (a), (b), (c), and (d) are present in an (a):(b):(c):(d) weight ratio of 25 to 65:0.1 to 5:10 to 50:10 to 50.

6. The process according to claim 2, wherein said oil phase $O_1$ is a dispersion comprising:
(a) fine metal oxide particles having ultraviolet screening ability;
(b) a polymer containing a hydrophobic monomer unit and a hydrophilic monomer unit;
(c) a silicone oil; and
(d) an alcohol having from 1 to 3 carbon atoms,
wherein said (a), (b), (c), and (d) are present in an (a):(b):(c):(d) weight ratio of 25 to 65:0.1 to 5:10 to 50:10 to 50.

7. The process according to claim 1, wherein said emulsifier (B) has an HLB of 7 or less.

8. The process according to claim 1, wherein in said emulsifier (B) the oxazoline unit and the polyoxyethylene unit are present in the respective macromer in an amount of from 10 to 40 wt. %.

9. The process according to claim 1, wherein said emulsifier (B) is present in an amount of from 0.01 to 10 wt. % based on the weight of the entire composition.

10. The process according to claim 1, wherein said emulsifier (B) is an oxazoline-modified silicone.

11. The process according to claim 10, wherein said oxazoline-modified silicone is a poly-N-acylethyleneimine-modified silicone.

12. The process according to claim 1, wherein said emulsifier (B) is a polyoxyethylene methylpolysiloxane copolymer.

* * * * *